(12) United States Patent
Perthu

(10) Patent No.: US 10,702,661 B2
(45) Date of Patent: Jul. 7, 2020

(54) INJECTION DEVICE

(71) Applicant: UNION MEDICO APS, København Ø (DK)

(72) Inventor: Michael Perthu, Copenhagen (DK)

(73) Assignee: UNION MEDICO APS, Copenhagen (DK)

( * ) Notice: Subject to any disclaimer, the term of this patent is extended or adjusted under 35 U.S.C. 154(b) by 546 days.

(21) Appl. No.: 15/123,636

(22) PCT Filed: Jan. 28, 2015

(86) PCT No.: PCT/DK2015/050019
§ 371 (c)(1),
(2) Date: Sep. 3, 2016

(87) PCT Pub. No.: WO2015/131903
PCT Pub. Date: Sep. 11, 2015

(65) Prior Publication Data
US 2017/0072142 A1 Mar. 16, 2017

(30) Foreign Application Priority Data

Mar. 6, 2014 (DK) .................................. 2014 70107
Aug. 26, 2014 (DK) .................................. 2014 70510

(51) Int. Cl.
*A61M 5/32* (2006.01)
*A61M 5/00* (2006.01)
*A61M 5/46* (2006.01)

(52) U.S. Cl.
CPC .......... *A61M 5/3202* (2013.01); *A61M 5/002* (2013.01); *A61M 5/3287* (2013.01); *A61M 5/46* (2013.01); *A61M 2207/00* (2013.01)

(58) Field of Classification Search
CPC .............. A61M 2207/00; A61M 5/002; A61M 5/3202; A61M 5/3287; A61M 5/46
See application file for complete search history.

(56) References Cited

U.S. PATENT DOCUMENTS

| 1,320,536 A | 11/1919 | DiFalco |
| 1,991,103 A | 2/1935 | King |

(Continued)

FOREIGN PATENT DOCUMENTS

| AU | 8704582 | 9/1983 |
| WO | 200141837 | 6/2001 |

(Continued)

OTHER PUBLICATIONS

WO Appln. No. PCT/DK2014/000040 (published as WO2015014363 and counterpart to U.S. Appl. No. 14/909,507), International Search Report, dated Mar. 25, 2015.

(Continued)

*Primary Examiner* — Brandy S Lee
(74) *Attorney, Agent, or Firm* — Maier & Maier, PLLC

(57) ABSTRACT

Disclosed is an injection device (1280) for injecting a hypodermic syringe (1260) along an injection direction defining an injection axis. The injecting device comprises a housing (1281) for being positioned at the skin and a movable element (1282) movably arranged relative to the housing between a retracted position and an injection position. The movable element comprises a hypodermic syringe holder (1289) for holding a hypodermic syringe. Disclosed is further a protective cover (1200) for a needle, and methods for arranging a hypodermic syringe in an injection device.

19 Claims, 8 Drawing Sheets

(56) References Cited

U.S. PATENT DOCUMENTS

| | | | |
|---|---|---|---|
| 2,295,849 A | 9/1942 | Kayden | |
| 2,664,086 A | 12/1953 | Transue | |
| 2,918,063 A | 12/1959 | Tucker | |
| 3,941,130 A | 3/1976 | Tibbs | |
| 4,787,891 A | 11/1988 | Levin | |
| 2006/0258990 A1* | 11/2006 | Weber | A61M 5/20 604/208 |
| 2011/0301534 A1 | 12/2011 | Renz | |

FOREIGN PATENT DOCUMENTS

| | | |
|---|---|---|
| WO | 2008131440 | 10/2008 |
| WO | 201501436 | 2/2015 |
| WO | 2015131903 | 9/2015 |

OTHER PUBLICATIONS

WO Appln. No. PCT/DK2014/000040 (published as WO2015014363 and counterpart to U.S. Appl. No. 14/909,507), International Preliminary Report on Patentability, dated Feb. 2, 2016.

WO Appln. No. PCT/DK2015/050019 (published as WO2015131903 and counterpart to instant appln), International Search Report and Written Opinion, dated Mar. 12, 2015.

WO Appln. No. PCT/DK2015/050019 (published as WO2015131903 and counterpart to instant appln), International Preliminary Report on Patentability, dated Sep. 15, 2016.

* cited by examiner

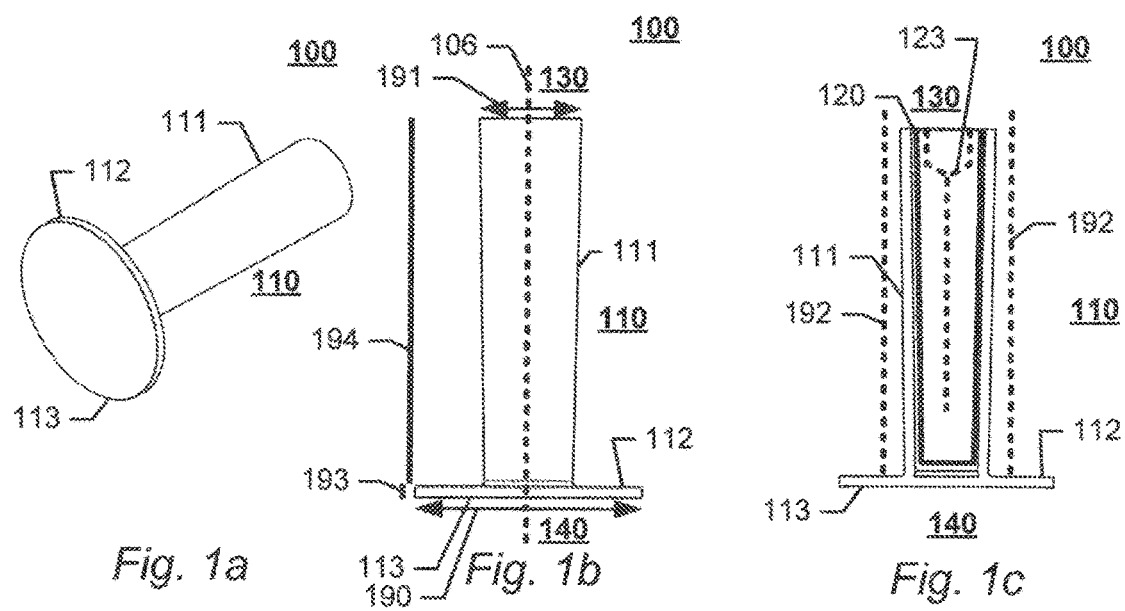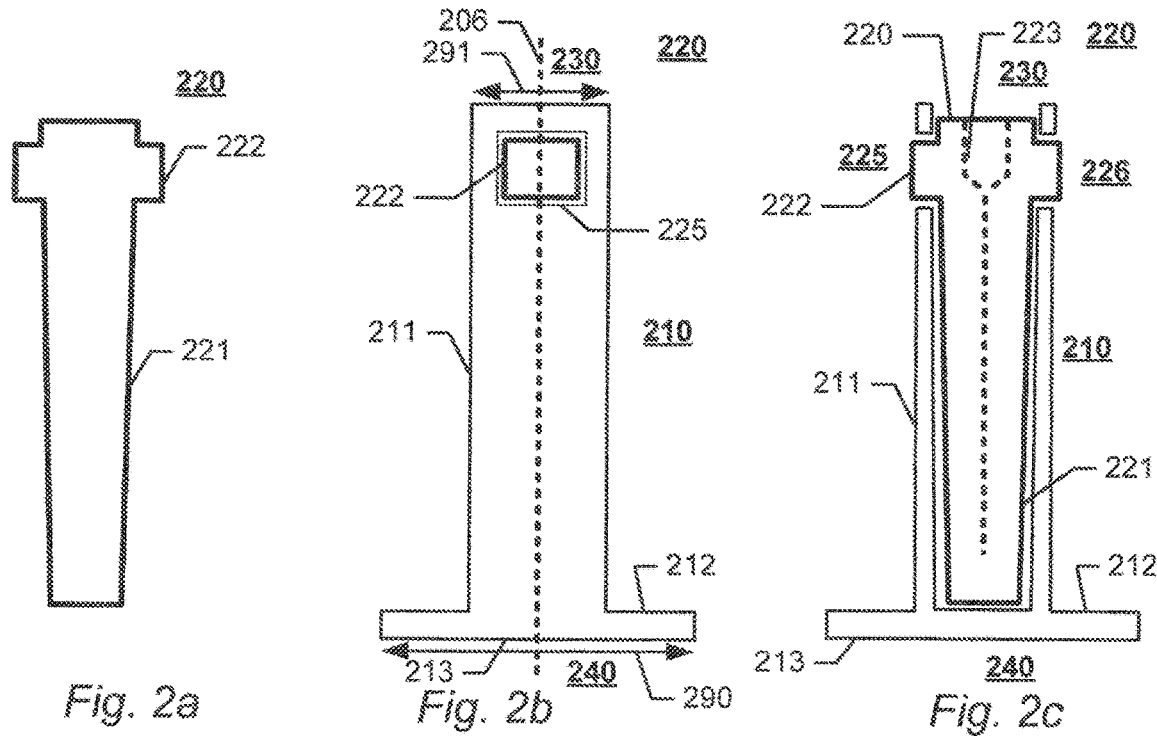

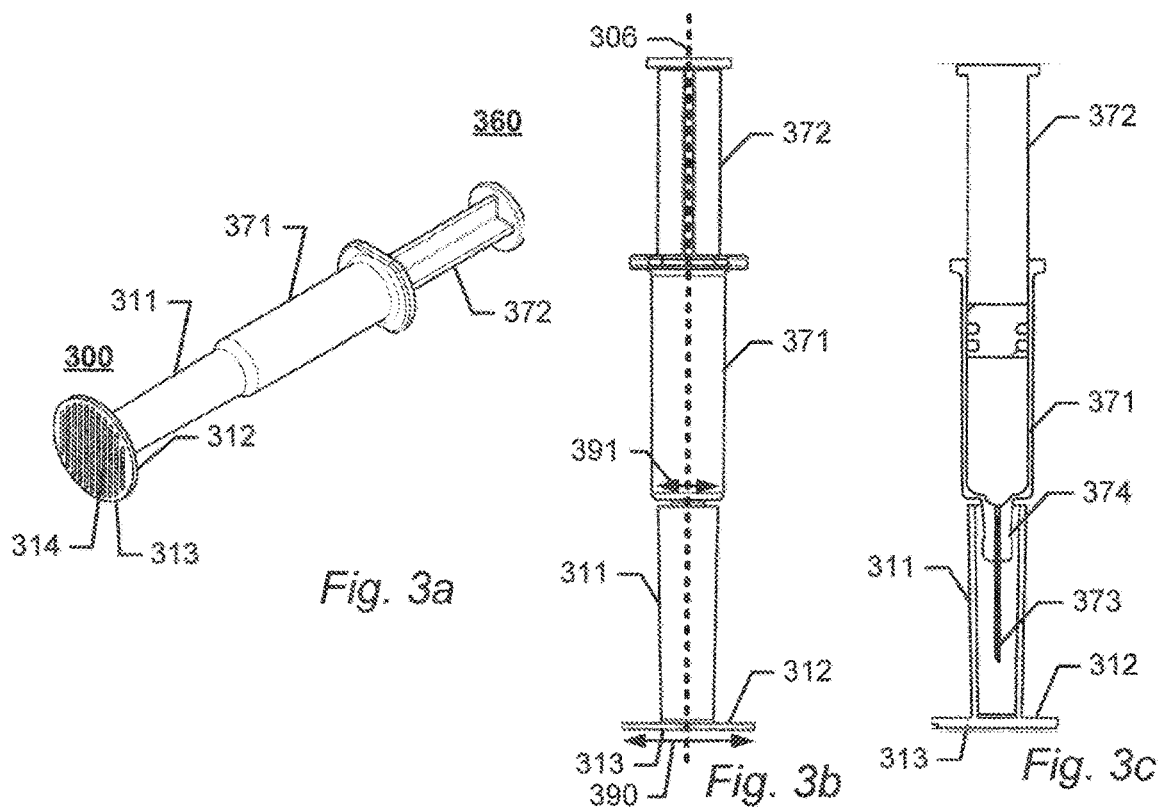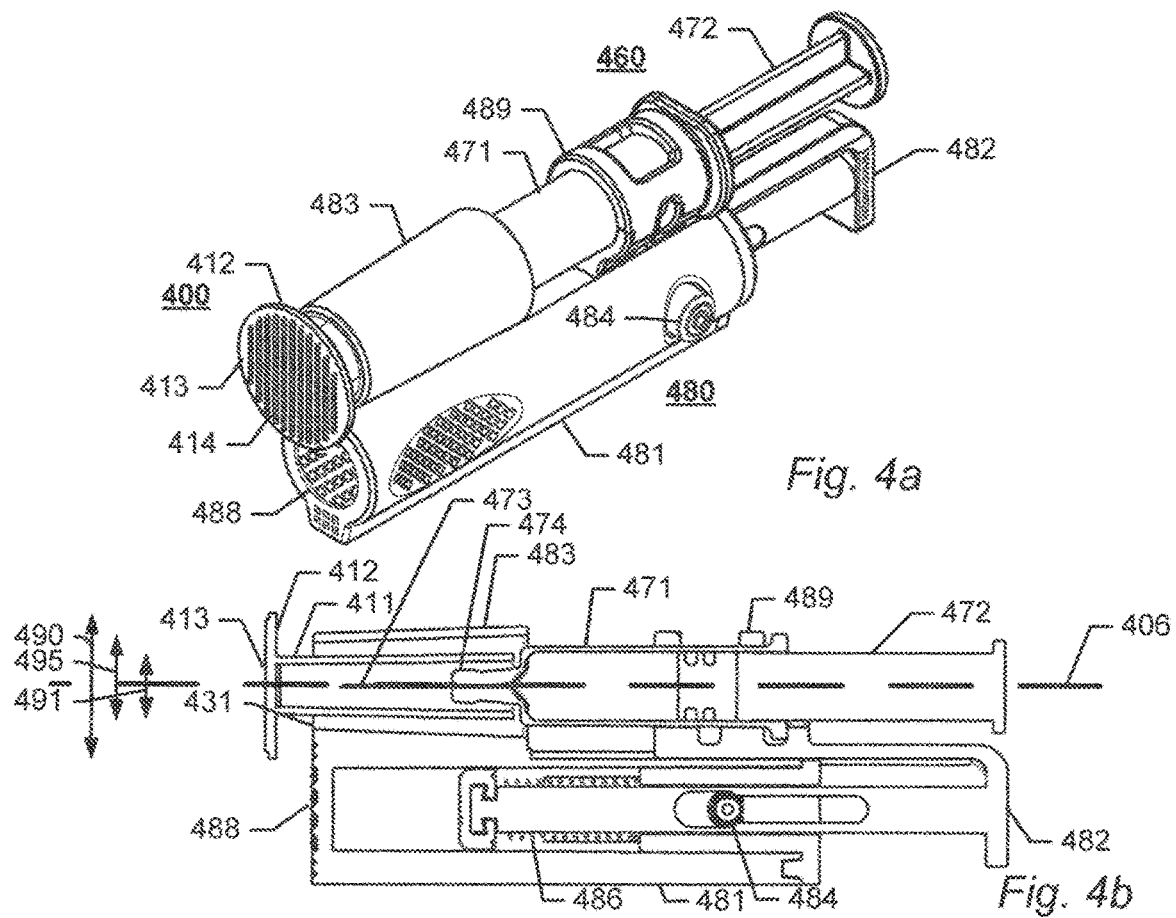

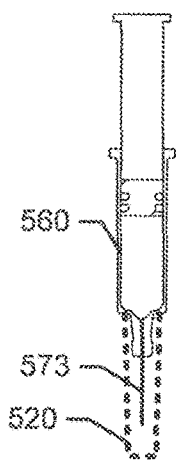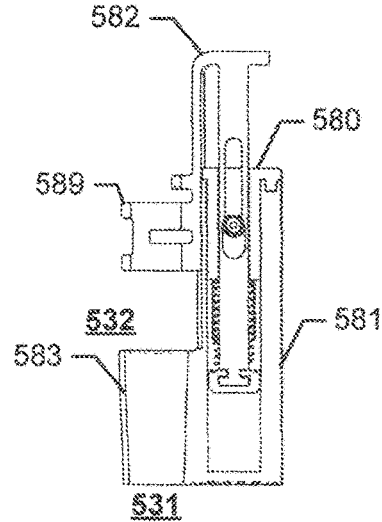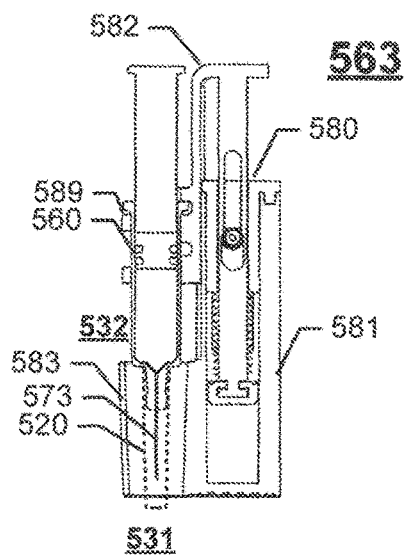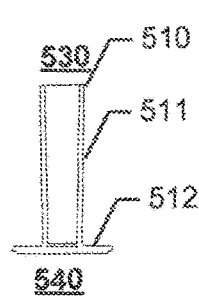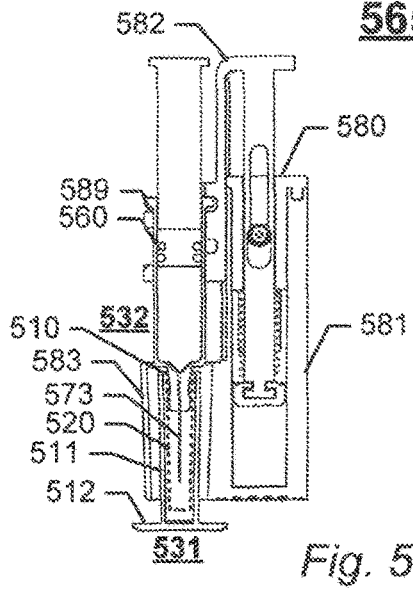
Fig. 5
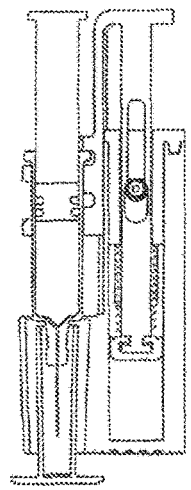
Fig. 6a
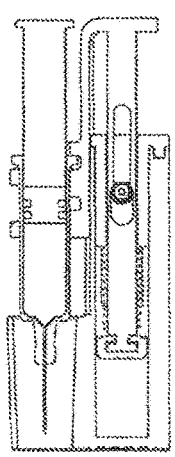
Fig. 6b
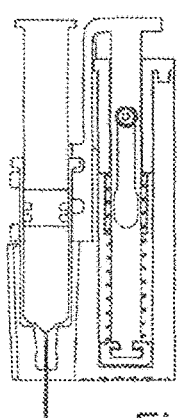
Fig. 6c

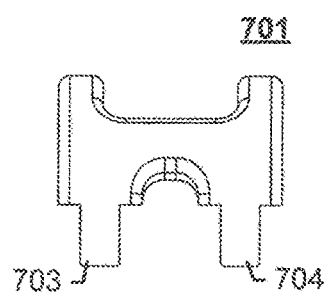
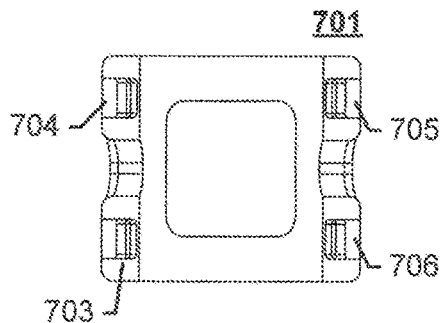
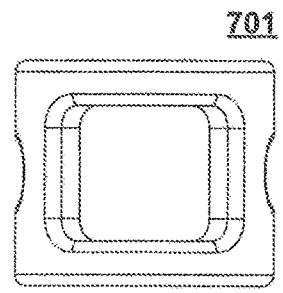
Fig. 7a    Fig. 7b    Fig. 7c
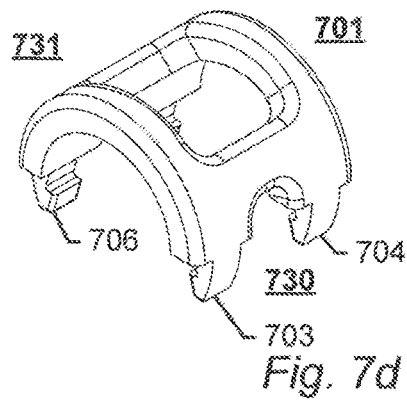
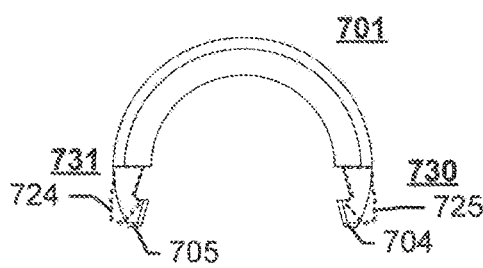
Fig. 7d    Fig. 7e
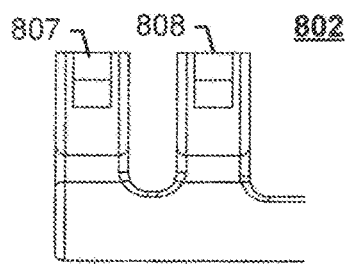
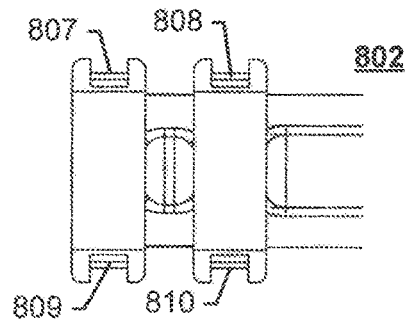
Fig. 8a    Fig. 8b
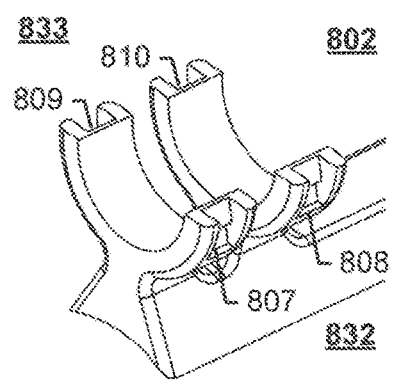
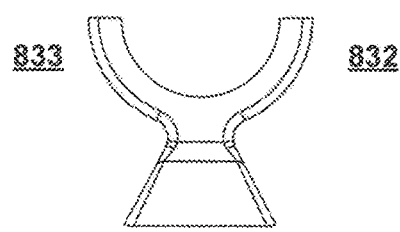
Fig. 8c    Fig. 8d

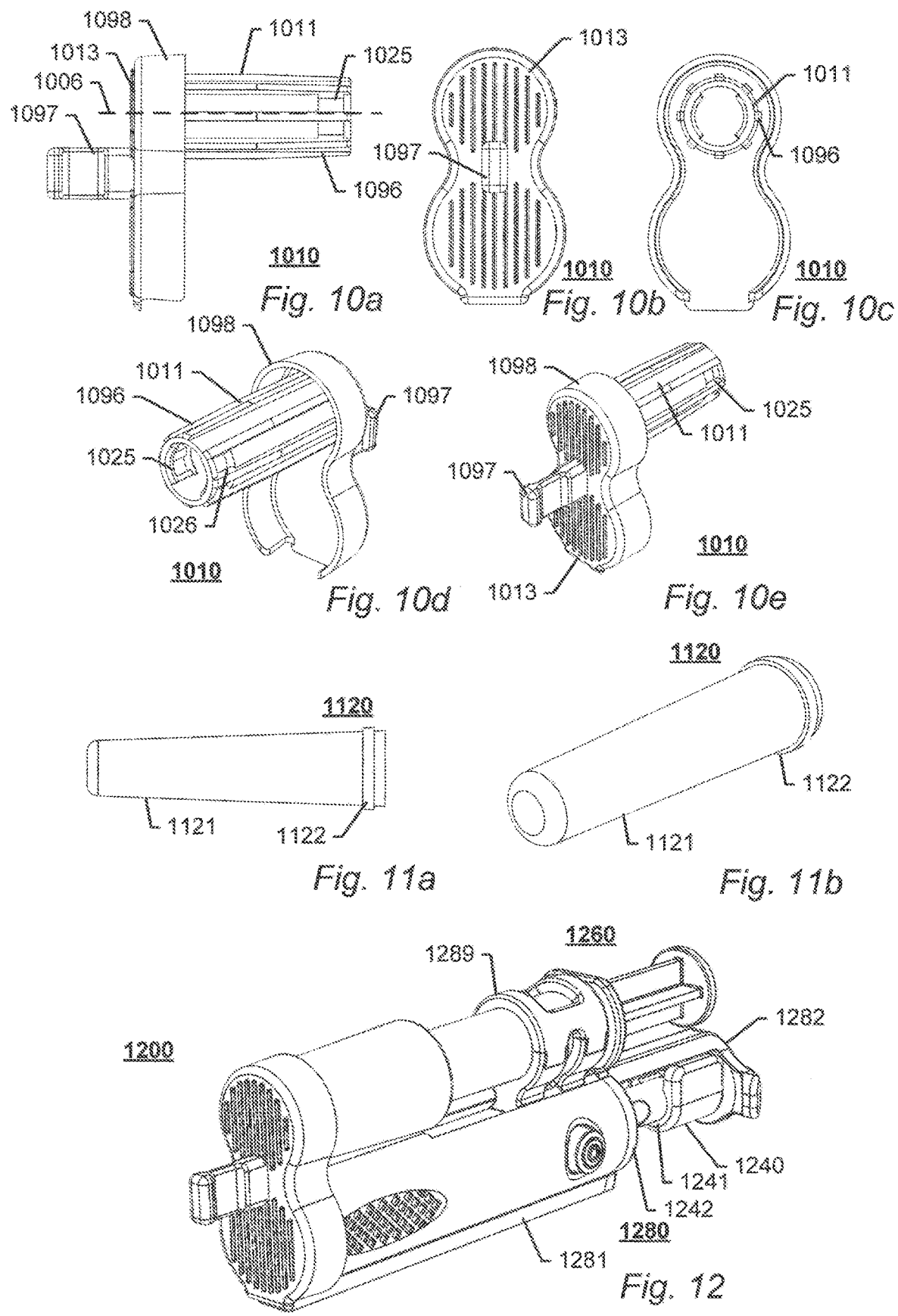

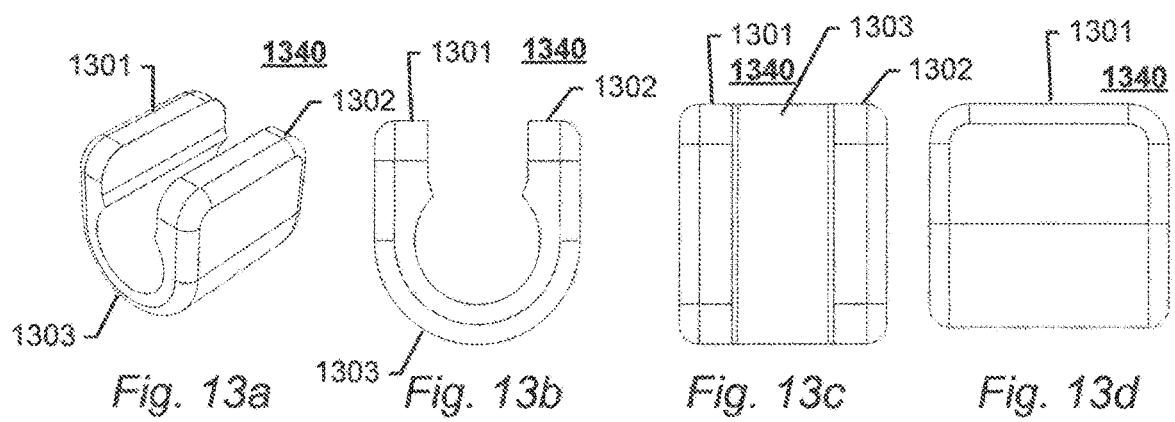
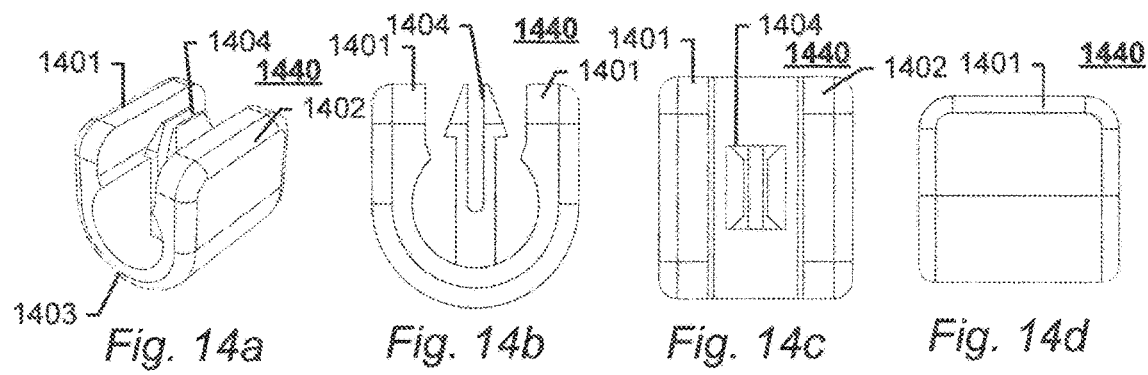
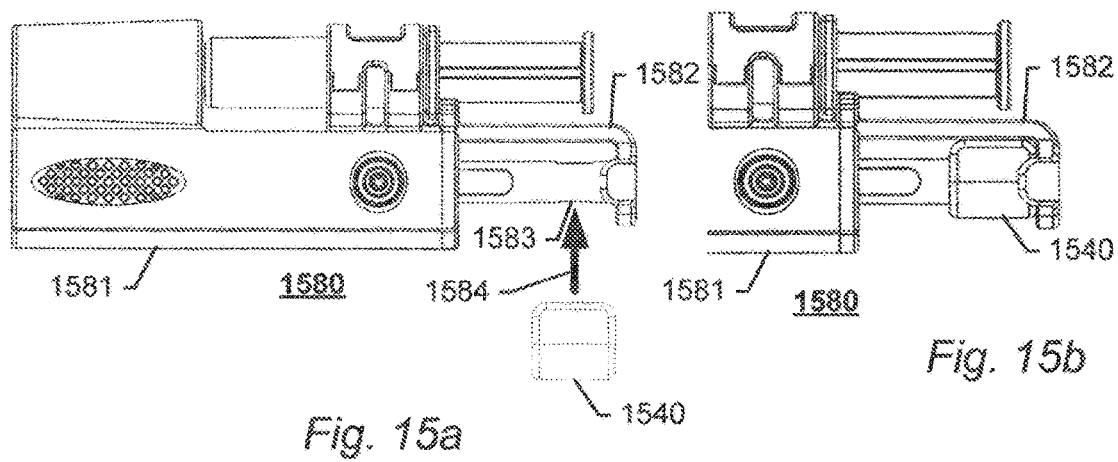
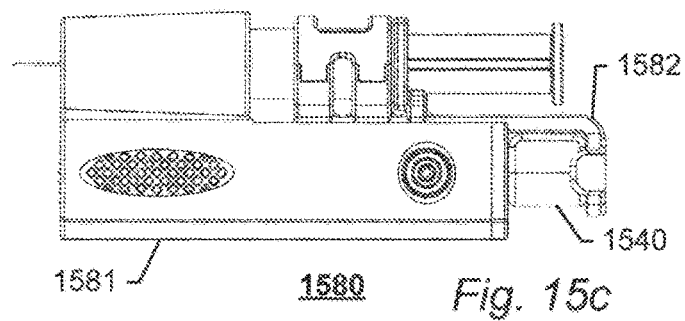

INJECTION DEVICE

FIELD

The present invention relates to an injection device, to a method of arranging a hypodermic syringe in an injection device, and to a protective cover.

BACKGROUND

Many people are faced with the task of injecting hypodermic syringes in their daily lives. The purpose of these injections may be for therapeutic treatment, prophylactic treatment or cosmetic treatment. Examples of therapeutic treatments are subcutaneous delivery of insulin for diabetics, subcutaneous delivery of epinephrine for people suffering from Anaphylaxis, intramuscular and/or subcutaneous delivery of antibiotics for treatment of infections, and intramuscular delivery of drugs for treatment of Multiple Sclerosis. Examples of prophylactic treatment are intramuscular delivery of vitamins, subcutaneous delivery of vaccines, and intramuscular and/or subcutaneous delivery of medicaments.

The injections may be performed by the users themselves or by medical professionals. In both cases it is desirable to secure that the injections are performed in a safe and controlled manner. This may be achieved by using an automatic injecting device configured to automatically inject a syringe.

To simplify the injection process, pre-filled syringes having a cover arranged around the needle are often used. The cover protects the needle and secures sterile conditions.

However, it may be difficult to:
remove a protective, especially for people having reduced hand functions such as people suffering from rheumatoid arthritis;
arrange a prefilled hypodermic syringe fitted with a cover in an automatic injection device; and
provide an automatic injection device that may be used by a large group of different users.

SUMMARY

According to a first aspect, the invention relates to an injection device for injecting a hypodermic syringe along an injection direction defining an injection axis, wherein said injecting device comprises:
a housing for being positioned at the skin, wherein said housing comprises a tubular element; and
a movable element movably arranged relative to said housing between a retracted position and an injection position, said movable element comprising: a hypodermic syringe holder for holding a hypodermic syringe; a first portion arranged to slide inside said tubular element of said housing; and a second portion arranged to slide outside said housing
wherein said hypodermic syringe holder comprises an upper part and a lower part, said lower part being attached to said second portion of said movable element, said upper part is configured for mechanically engaging with said lower part, and together with said lower part surround said hypodermic syringe and prevent said hypodermic syringe from moving relative to said movable element.

Consequently, by using a holder that surrounds the hypodermic syringe, the hypodermic syringe may effectively and securely be attached to the movable element. Furthermore, by using a holder comprising two parts the hypodermic syringe may easily be fitted within the holder.

The housing and/or the movable element may be made of plastic. The housing and the movable element may be practically non-deformable during normal use, i.e. the housing and the movable element may deform less than 5% during normal use. The injection device may be configured to allow a user to manually operate a plunger of a hypodermic syringe arranged in the hypodermic syringe holder. The injection device may be a single use injection device. The injection device may comprise a release mechanism for initiating an injection of the hypodermic syringe. The injection device may be configured so that when said movable element is in said retracted position and said release mechanism is pushed said movable element moves to said injection position whereby a hypodermic syringe attached to said hypodermic syringe holder may be injected.

The second portion may be configured to slide at a first outer surface of said housing. The first portion and the second portion may be connected through a connection portion. The movable element may extend out of an upper opening of the tubular element of the housing. Alternatively, the connection portion may extend through an elongated slit in the tubular element of the housing. The lower part of the hypodermic syringe holder, the first portion, the second portion and the connection portion of the movable element may be integrally moulded as a single element. Alternatively, the lower part may be adhered to the second portion of the movable element.

The upper part may be completely separate from the lower part until the upper part is mechanically engaged with the lower part. Alternatively, the upper part may be connected to the lower part via a hinge i.e. the upper part may be rotated from an open position, where the upper part is not mechanically engaged with the lower part, to a closed position where the upper part is mechanically engaged with the lower portion.

The movable element may comprise a first portion arranged to slide inside the tubular element of the housing, a second portion arranged to slide at a first outer surface of said housing, and a connection portion connecting said first portion with said second portion, wherein said movable element extends out of said upper opening of said first tubular element.

In some embodiments, said hypodermic syringe holder comprises a groove configured for receiving a collar of said hypodermic syringe whereby said hypodermic syringe is prevented from moving relative to said movable element.

Consequently, the hypodermic syringe may in an effective manner be prevented from moving relative to the movable element. The use of the two part hypodermic syringe holder, will furthermore make it simpler to arrange the collar of the syringe in the groove.

In some embodiment, said groove is positioned so that the collar of said hypodermic syringe can only be arranged in said groove before said upper part is mechanically engaged with said lower part.

In some embodiments, the upper part is configured to mechanically engage with the lower part using a male/female locking mechanism wherein the male part comprises a protruding member and the female part comprises a recess and/or opening.

Consequently, the upper part may in an easy manner be mechanically engaged with said lower part.

The upper part of the hypodermic syringe holder may be the male part and the lower part may be the female part. Thus, the upper part may comprise a protruding member and the lower part may comprise a recess and/or opening. Alternatively, the upper part may be the female part and the lower part may be the male part, whereby the upper part may comprise a recess and/or opening and the lower part may comprise a protruding member.

In some embodiments, the male/female locking mechanism is configured to permanently mechanically engage said upper part with said lower part thereby preventing said upper part from being disengaged with said lower part without damaging the injection device.

Consequently, it may be secured that a single use injection device is not re-used multiple times. This will increase the safety of both the patient and the operator of the injection device.

In some embodiments, the protruding member of the male part (the upper part or the lower part) is a flexible protruding member configured to deform from a first shape to a second shape when the male part comes into contact with the female part, and further to snap back into approximately the first shape when the flexible protruding member is aligned with the recess and/or opening of the female part, whereby the flexible protruding member engages with the recess and/or opening and locks the male part to the female part, allowing the upper part to be attached to the lower part by a pure translation between the two.

Consequently, an easy and secure method of mechanically engaging the upper part with the lower part is provided. This may further make it easier to automate the process of mechanically engaging the upper part with the lower part, e.g. enabling pre-filled hypodermic syringe to be arranged in the hypodermic syringe holder in an automated process.

In some embodiments, both the male part and the female part have a first side and a second side opposite to the first side, wherein the male part has a first flexible protruding member at said first side and a second flexible protruding member at said second side and the female part has a first opening/recess at said first side and a second opening/recess at said second side.

Consequently, the upper part may more securely be attached to the lower part.

In some embodiments, the male part has a third flexible protruding member at said first side and a fourth flexible protruding member at said second side, and said female part has a third opening/recess at said first side and a fourth opening/recess at said second side.

Consequently, rotational movement of the hypodermic syringe relative to the hypodermic syringe holder may more effectively be prevented.

In some embodiments, the hypodermic syringe holder further comprises a second upper part and a second lower part, the second upper part and the second lower part being arranged with a distance to the (first) lower part and (first) upper part.

Consequently, hypodermic syringes may more effectively be secured to the hypodermic syringe holder. This further allows larger hypodermic syringes to be used.

The second lower part may be an upper part as disclosed above. Correspondingly, the second upper part may be an upper part as disclosed above.

According to a second aspect the invention relates to a set comprising an injection device as disclosed in relation to the first aspect of the invention and a hypodermic syringe having a needle, the hypodermic syringe being arranged in said hypodermic syringe holder, the upper part of the hypodermic syringe holder is mechanically engaged with the lower part, and wherein the hypodermic syringe was arranged on the lower part of the hypodermic syringe holder before the upper part of the hypodermic syringe holder became mechanically engaged with the lower part.

In some embodiments, said tubular element of said injection device has a needle shield attached, the tip of the needle of said hypodermic syringe being fully arranged inside said needle shield, when the movable element is arranged in the retracted position.

In some embodiments, the set further comprises a protective cover s disclosed in relation to the fourth aspect of the invention, wherein said protective cover is arranged around said needle of said hypodermic syringe.

According to a third aspect, the invention relates to a method of arranging a hypodermic syringe in an injection device, said method comprises the steps of:
  obtaining a hypodermic syringe having a needle;
  obtaining an injection device as disclosed in relation to the first aspect of the invention with the upper part of the hypodermic syringe holder being mechanically disengaged from the lower part;
  arranging said hypodermic syringe in the lower part of the hypodermic syringe holder;
  mechanically engaging said upper part with said lower part whereby said hypodermic syringe is prevented from moving relative to said movable element of said injection device.

Consequently, a simple and secure method of arranging a hypodermic syringe in an injection device is provided.

In some embodiments, said upper part is being mechanically engaged with said lower part by a pure translation between the two.

Thus the upper part may be mechanically engaged with the lower part by keeping the injection device stationary and lowering the upper part upon the lower part.

In some embodiments, the hypodermic syringe is a pre-filled hypodermic syringe having an inner member of a protective cover arranged around its needle, the injection device is an injection device having a needle shield attached to said tubular element, said needle shield having a first opening for facing the skin of the user and a second opening opposite to said first opening and wherein the method further comprises the steps of:
  obtaining an outer member of said protective cover having a first end and a second end opposite to said first end, said outer member comprises an elongated tubular body part having an opening at said first end, and a terminal part arranged at the second end, said terminal part having a widest width larger than the widest width of the elongated tubular body part;
  arranging said outer member around said inner member by inserting said outer member through said first opening of the needle shield so that said terminal part is arranged outside said needle shield;
wherein said outer member is configured to grip said inner member, whereby said inner member is secured to said outer member thereby allowing a user to remove both said inner member and said outer member of said protective cover from said needle by pulling in the terminal part.

Consequently, a simple and secure method of arranging a prefilled hypodermic syringe in an injection device is provided. Furthermore, the use of a two component needle cap: enables the terminal part of the outer component to have a widest width, large than the widest with of the needle shield; and reduces the requirement to the facility where the pre-filed hypodermic syringe in arranged in the injection device. Furthermore, the risk that the needle is damaged when the needle cap is arranged around it may be lowered as the inner member will stiffen and protect the needle.

According to a fourth aspect, the invention relates to a protective cover for a needle of a hypodermic syringe, said protective cover has an first opening at a first end for receiving the needle and a second end opposite to the first end, wherein said protective cover comprises an outer member for allowing a user to grip said outer member and remove said protective cover from said needle, said outer member has an elongated body part and a terminal part, said terminal part is arranged at the second end of the protective cover wherein said terminal part has a widest width larger than the widest width of said elongated body part, said terminal part being configured to allow a user to grip said terminal part and remove said protective cover when said body part is completely positioned inside a tubular protective element such as a needle shield of an injection device.

Consequently, by providing the protective cover with an outer member having a wide terminal part a protective cover for a needle that is easier to operate is provided.

The outer member is preferably made of a rigid material such as a rigid plastic material. The needle is preferably inserted in the centre of the protective cover along a central axis of the protective cover. The elongated body part of the outer member is preferably extending along the central axis.

The terminal part may have a height along the central axis substantial shorter than the height of the elongated body part e.g. less than 20%, 10% or 5% of the height of the elongated body part. The widest width of the terminal part and the elongated body part is measured in planes being perpendicular to the central axis. The terminal part may be formed as a plate extending in a plane being perpendicular to the central axis. The plate may have any shape such as a rectangular, quadratic, or circular shape.

In some embodiments, said terminal part has a support surface facing away from the needle, said support surface is configured to allow a hypodermic syringe connected to a needle arranged in the protective cover to stand vertically.

Consequently, a plurality of pre-filled hypodermic syringes may be securely stored in a limited space such as a bathroom cabinet.

In some embodiments, said support surface covers/encloses an area 1.2 times, 1.5 times, 2 times or 4 times larger than the area of the first end of the protective cover.

Consequently, a stable support surface may be provided.

The support surface is extending in a plane being perpendicular to the central axis.

In some embodiments, said support surface has a plurality of protruding elements for preventing the support surface from sliding.

In some embodiments, said elongated body part is an elongated tubular body part extending along a central axis, said protective cover further comprises an inner member arranged inside and secured to said elongated tubular body part so that both said outer member and said inner member are removed from said needle when a user pulls in said terminal part of said outer member.

The inner member may be made of a flexible material such as a rubber or a rubber like material. The inner member may have an opening for receiving the needle. Alternatively, the inner member may be made of a material configured to be penetrated by the needle without damaging the needle.

In some embodiments, said outer member has a aperture, said inner member has a griping element extending into said aperture of said outer member, wherein said griping element is configured to secure said inner member to said outer member so that both said outer member and said inner member are removed from said needle when a user pulls in said terminal part of said outer member.

The aperture may be provided in the top of the outer member and extending along the central axis of the protective cover. The gripping element of the inner member may be collar arranged at the top of the inner member. The outer member may comprise a plurality of apertures e.g. at least 2, 3 or 4 apertures.

In some embodiments, the elongated tubular body part comprises a plurality of guiding protrusions protruding from an outer surface of the elongated tubular body part and extending along the central axis.

Consequently, it may become easier to arrange the elongated tubular body part inside a tubular needle shield of an injection device.

The guiding protrusions may be configured to align the protective cover with a needle arranged inside a tubular needle shield of an injection device.

In some embodiments, said terminal part comprises a plate having an inner surface facing the needle and an outer surface opposite to the inner surface, wherein said inner surface has a first portion and a second portion, said elongated tubular body part protrudes from said first portion, and said second portion surrounds said first portion and is configured to close an opening of a tubular needle shield of an injection device.

Consequently, by closing the needle shield the protective cover may be used to shield of the needle after is has been used for providing an injection whereby the exposure hazard from body fluids on the needle may be limited.

The plate may extend in a plane being perpendicular to the central axis.

In some embodiments, the terminal part further comprises a wall protruding from the circumference of the plate, said wall having an inner surface for abutting an outer surface of an injection device and frictionally gripping said outer surface of said injection device, whereby said protective cover may be attached simultaneously to said needle and the injection device.

Consequently, a protective cover may more efficiently and safely close the needle shield.

In some embodiments, said terminal part further comprises a handle protruding from the outer surface of the plate.

Consequently, the handle may enable the protective cover to be both easier removed and re-inserted over the needle. By providing the handle on the outer surface of the plate of the terminal part, the exposure hazard for medical professionals may be reduced when the protective cover is re-insert over a used needle, as the plate will protect for droplets from the needle.

In some embodiments, the plate has a widest width being at least 1.5 times larger than the widest width of the elongated tubular body part, wherein the handle is protruding with a distance to the central axis.

Consequently, the exposure hazard may be even further reduced.

According to a fifth aspect the invention relates to a set comprising a protective cover as disclosed in relation to the fourth aspect, and a hypodermic syringe having a needle, wherein said protective cover is arranged around said needle.

In some embodiments, the set further comprises an injection device for injecting a hypodermic syringe along an injection direction defining an injection axis, wherein said injecting device comprises:

a housing for being positioned at the skin, wherein said housing comprises an elongated main body; and a movable element movably arranged relative to said housing between a retracted position and an injection position, wherein said movable element comprises a hypodermic syringe holder for holding a hypodermic syringe;

wherein said hypodermic syringe is arranged in said hypodermic syringe holder.

The injection axis and the central axis are same axis. The housing and/or the movable element may be made of plastic. The housing and the movable element may be practically non-deformable during normal use, i.e. the housing and the movable element may deform less than 5% during normal use. The syringe holder may be detachable connected to the movable element, whereby it can be exchanged allowing the same injection device to be used together with hypodermic syringes of different sizes. The injection device may comprise a release mechanism for initiating an injection of the hypodermic syringe. The injection device may be configured so that when said movable element is in said retracted position and said release mechanism is pushed said movable element moves to said injection position whereby a hypodermic syringe attached to said hypodermic syringe holder may be injected. The injection device may be configured to allow a user to manually operate a plunger of a hypodermic syringe arranged in the hypodermic syringe holder.

In some embodiments, said elongated body of said injection device has a needle shield attached, said elongated body of said protective cover being at least partly arranged inside said needle shield, and said terminal part being arranged outside said needle shield whereby a user may easily grip said terminal part and remove said protective cover from said needle.

Consequently, the set is both easy to operate and protects the user from being stung. This is especially important when the user is a medical professional as it reduces the risk of infecting the medical professional with infectious diseases such as HIV or Hepatitis.

The needle shield may comprise a first opening facing the skin of a user when the injection device is positioned at the skin of the user. The housing may comprise a planar contact surface for being positioned at the skin of a user, wherein the first opening forms part of said planar contact surface. The needle shield may be a tubular needle shield.

The needle shield may be attached to an outer side of the elongated body. The needle shield may further comprise a second opening opposite to the first opening.

In some embodiments, said housing comprises a gripping zone, said needle shield forms part of said gripping zone and wherein said gripping zone is configured to allow a user to safely hold said injection device at any position of said gripping zone while a hypodermic syringe is being injected.

According to a sixth aspect the invention relates to a method of arranging a pre-filled hypodermic syringe in an injection device, said method comprises the steps of:
 obtaining a pre-filled hypodermic syringe having a needle, wherein an inner member of a protective cover is arranged around said needle;
 obtaining an injection device for injecting a hypodermic syringe along an injection direction defining an injection axis, wherein said injecting device comprises:
  a housing for being positioned at the skin, wherein said housing comprises an elongated main body having a needle shield attached, said needle shield having a first opening for facing the skin of the user and a second opening opposite to said first opening; and
  a movable element movably arranged relative to said housing between a retracted position and an injection position, wherein said movable element comprises a hypodermic syringe holder for holding a hypodermic syringe;
 arranging said pre-filled hypodermic syringe in the hypodermic syringe holder of said injection device so that said inner member is at least partly arranged inside the needle shield of the injection device;
 obtaining an outer member of said protective cover having a first end and a second end opposite to said first end, said outer member comprises an elongated tubular body part having an opening at said first end, and a terminal part arranged at the second end, said terminal part having a widest width larger than the widest width of the elongated tubular body part;
 arranging said outer member around said inner member by inserting said outer member through said first opening of the needle shield so that said terminal part is arranged outside said needle shield;

wherein said outer member is configured to grip said inner member, whereby said inner member is secured to said outer member thereby allowing a user to remove both said inner member and said outer member of said protective cover from said needle by pulling in the terminal part.

Consequently, an efficient method of arranging a pre-filled hypodermic syringe fitted with a protective cover in an injection device is provided.

Thus, both the syringe and the injection device may be disposable.

As the pre-filled hypodermic syringe is obtained with the inner member of the protective cover arranged around the needle (securing sterile conditions), the requirements to the environment where the pre-filled hypodermic syringe is arranged in the hypodermic syringe holder may be less strict.

In some embodiments, the widest width of the needle shield is smaller than the widest width of the terminal part of the outer member of the protective cover.

By using a protective cover comprising two members, the outer member may have a widest width being larger than the widest width of the needle shield. This will make it easier for the user to remove the protective cover from the needle.

According to a seventh aspect, the invention relates to an injection device for injecting a hypodermic syringe along an injection direction defining an injection axis, wherein said injecting device comprises:
 a housing for being positioned at the skin; and
 a movable element movably arranged relative to said housing between a retracted position and an injection position, said movable element comprising: a hypodermic syringe holder for holding a hypodermic syringe;
wherein said injection device further comprises an injection depth modifying element configured to modify the injection depth of the injection device.

Consequently, a more versatile injection device is provided that may be used by a broader group of users and for a broader group of purposes.

As an example the injection depth modifying element may enable the injection device to be used for making intra muscular injections for patients having different fat layer thicknesses. Furthermore, injections may be performed at precise depths enabling precise delivery of a drug to a predetermined target e.g. if a tumour has been located using a medical imaging modality such as CT of ultrasound, the injection depth modifying element may be used to secure that a drug is delivered to the tumour or in a desired proximity to the tumour.

The housing and/or the movable element may be made of plastic. The housing and the movable element may be practically non-deformable during normal use, i.e. the housing and the movable element may deform less than 5% during normal use. The syringe holder may be detachable connected to the movable element, whereby it can be exchanged allowing the same injection device to be used together with hypodermic syringes of different sizes. The injection device may comprise a release mechanism for initiating an injection of the hypodermic syringe. The injection device may be configured so that when said movable element is in said retracted position and said release mechanism is pushed said movable element moves to said injection position whereby a hypodermic syringe attached to said hypodermic syringe holder may be injected. The injection device may be configured to allow a user to manually operate a plunger of a hypodermic syringe arranged in the hypodermic syringe holder. The injection device may have a needle shield attached.

The needle shield may be attached to an outer side of the elongated body.

In some embodiments, said injection depth modifying element is movable relative to both said housing and said movable element and being attachable at a first position to a selected element selected from the group of elements consisting of said movable element and said housing, wherein when said injection depth modifying element is attached at said first position the movable element is limited to be movable relative to the housing between the retracted position and an intermediate position whereby the injection depth is reduced.

Consequently, a simple injection device that is easy to manufacture and capable of adapting the injection depth to specific needs is provided The distance between the intermediate position and the retracted position is smaller than the distance between the retracted position and the injection position. The injection depth modifying element may be permanently or non-permanently attached to said selected element at said first position.

In some embodiments, said selected element is the movable element; said housing comprises: a tubular element having an upper opening; and said movable element comprises: a first portion arranged to slide inside said tubular element of said housing, a second portion arranged to slide outside said housing and a connection portion connecting said first portion with said second portion, wherein said movable element extends out of said upper opening of said tubular element.

Consequently, an injection device having a simple design is provided.

In some embodiments, said housing comprises an upper surface facing away from the skin of the user; said injection depth modifying element comprises a lower surface facing said upper surface when said injection depth modifying elements is attached at said first position and wherein said lower surface of the injection depth modifying element abuts the upper surface of the housing when the movable element is in the intermediate position.

In some embodiments, said injection depth modifying element is attachable to said selected element at a plurality of positions.

Consequently, an injection device capable of adjusting the injection depth to three or more different depths is provided.

In some embodiments, said injection depth modifying element is permanently connected to said selected element and is movably arranged relative to said selected element along a first part of said selected element between a second position and the first position.

Consequently, the injection depth may precisely be selected.

The selected element is preferably the movable element, but it may also be the housing. The injection depth modifying element may be attachable to the selected element at any position between the second position and the first position.

In some embodiments, said first part of said selected element is provided with a scale for allowing a user to select a desired injection depth.

Consequently, a user may in an easy manner precisely select a desired injection depth.

A scale is to be understood as a sequence of marks representing different injection depths. The injection depth modifying element may comprise a pointer for pointing at the scale.

In some embodiments, the injection depth modifying element comprises a first element for surrounding at least a part of the selected element, and a second element for attaching the first element to the selected element, wherein the second element is movably arranged relative to the first element between an unengaged position and an engaged position, wherein the first element is movable relative to the selected element when the second element is in the unengaged position and attached to the selected element when the second element is in the engaged position.

In some embodiments, said injection depth modifying element is movably arranged relative to both said housing and said movable element between a detached position, where the injection depth modifying element is provided separate from the housing and the movable element, and the first position where the injection depth modifying element is attached to the selected element.

Consequently, an injection depth modifying element is provided that is both simple to manufacture and operate.

The injection depth modifying element may be attachable at a plurality of positions of the selected element. The injection depth modifying element may be permanently attached or non-permanently attached to the selected element e.g. if the selected element is the movable element and the injection depth modifying element is attached at the first position of the movable element it may be permanently attached to the movable element at the first position.

In some embodiments, the injection depth modifying element has a first gripping arm and a second gripping arm opposite to said first gripping arm, said first gripping arm and said second gripping arm being connect by a connection portion, wherein said first gripping arm and said second gripping arm are configured to receive said selected element and attach said injection depth modifying element to said selected element.

In some embodiments, the injection depth modifying element is attachable to the selected element at the first position by a male/female locking mechanism.

Consequently, the injection depth modifying element may be strongly attached to the selected element.

The selected element may be the female part and the injection depth modifying element may be the male part e.g. the selected element may have an opening configured to receive a protruding member of the injection depth modifying element. The selected element may have a plurality of opening configured to receive the protruding member of the injection depth modifying element. Alternatively, she selected element may be the male part and the injection depth modifying element may be the female part.

In some embodiments, said injection device further comprise a display, an input mechanism and an actuator, wherein said input mechanism is configured to allow a user to a select desired injection depth, said display is configured to display the selected injection depth and said actuator is configured to move said injection depth modifying element so that the selected desired injection depth results.

Consequently, an injection device that is precise and easy to operate is provided.

According to an eight aspect the invention relates to a set of elements comprising an injection device as disclosed in relation to any one of the embodiments of the seventh aspect and a pre-filled hypodermic syringe having a needle arranged in the hypodermic syringe holder of the injection device.

In some embodiments, the set further comprises a first injection depth modifying element movably arranged relative to both said housing and said movable element between a detached position, where the injection depth modifying element is provided separate from the housing and the movable element, and the first position where the injection depth modifying element is attached to the selected element wherein when said injection depth modifying elements is attached to said selected element, the movable element is limited to be movable relative to the housing between the retracted position and a first intermediate position In some embodiments, the set comprises second injection depth modifying element movably arranged relative to both said housing and said movable element between a detached position, where the injection depth modifying element is provided separate from the housing and the movable element, and attached position where the injection depth modifying element is attached to the selected element, wherein when said second injection depth modifying elements is attached to said selected element, the movable element is limited to be movable relative to the housing between the retracted position and a second intermediate position.

Consequently, a simple highly adaptable injection device is provided that can be set to at least three different injection depths.

The second injection depth modifying element may simply have a different size than the first injection depth modifying element e.g. it may be higher or lower.

In some embodiments, the set further comprises a protective cover as disclosed in relation to any one of the embodiments of the fourth aspect of the invention, wherein the protective cover is arranged around the needle of the pre-filled hypodermic syringe.

In some embodiments, the set is configured for single use and is packaged in a protective environment such as a plastic box closed by a plastic film.

The different aspects of the present invention can be implemented in different ways including as injection devices, protective covers, sets comprising protective covers, pre-filled hypodermic syringes and injection devices, and to methods of arranging a hypodermic syringe in an injection device as described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims.

Furthermore, it will be appreciated that embodiments described in connection with one of the aspects described herein may equally be applied to the other aspects. Specifically the protective cover obtained in embodiments described in connection with the sixth aspect may preferably be a protective cover as disclosed in relation to embodiments of the fourth aspect of the invention, and the injection device obtained in the embodiments described in connection with the sixth aspect may preferably be an injection device as disclosed in relation to the embodiments of the fifth aspect of the invention.

BRIEF DESCRIPTION OF THE DRAWINGS

The above and/or additional objects, features and advantages of the present invention will be further elucidated by the following illustrative and non-limiting detailed description of embodiments of the present invention, with reference to the appended drawings, wherein:

FIG. 1a-c show a protective cover according to an embodiment of the present invention.

FIG. 2a-c show a protective cover according to an embodiment of the present invention.

FIG. 3a-c show a set comprising a protective cover and a hypodermic syringe according to an embodiment of the invention.

FIG. 4a-b show a set comprising a protective cover, a hypodermic syringe and an injection device, according to an embodiment of the invention FIG. 5 illustrates a method of arranging a pre-filled hypodermic syringe in an injection device according to an embodiment of the invention.

FIG. 6a-c show how a set comprising an injection device, a pre-filled hypodermic syringe, and a protective cover for a needle may be used according to an embodiment of the invention.

FIG. 7a-e show an upper part of a hypodermic syringe holder according to an embodiment of the invention.

FIG. 8a-d show a lower part of a hypodermic syringe holder according to an embodiment of the invention.

FIG. 10a-e show an outer member of a protective cover according to an embodiment of the invention.

FIG. 11a-b show an inner member of a protective cover according to an embodiment of the invention.

FIG. 12 shows a set comprising a protective cover, a hypodermic syringe and an injection device, according to an embodiment of the invention.

FIG. 13a-d show an injection depth modifying element according to an embodiment of the invention.

FIG. 14a-d show an injection depth modifying element according to an embodiment of the invention.

FIG. 15a-c illustrate how an injection depth modifying element as shown in FIG. 14a-d may be attached to a selected element according to an embodiment of the invention.

DETAILED DESCRIPTION

Figure 9A:
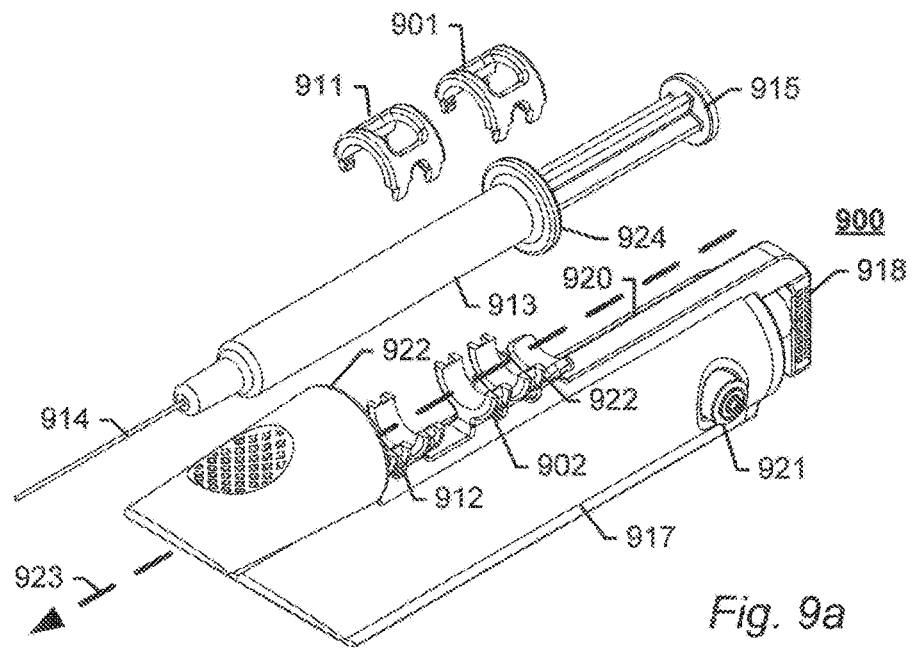
FIG. 9a-c show a set comprising an injection device and a hypodermic syringe according to an embodiment of the invention.

In the following description reference is made to the accompanying figures, which show by way of illustration how the invention may be practiced.

FIG. 1a-c show a protective cover for a needle of a hypodermic syringe according to an embodiment of the present invention. FIG. 1a shows a perspective view, FIG. 1b shows a side view, and FIG. 1c shows a cross-section along the central axis 106 shown in FIG. 1b. The protective cover 100 has a first opening 123 at a first end 130 for receiving the needle and a second end 140 opposite to the first end 130. The needle is inserted in the centre of the protective cover 100 along a central axis 106 of the protective cover 100. The protective cover 100 comprises an outer member 110 for allowing a user to grip the outer member 110 and remove the protective cover 100 from the needle. The outer member 110 has an elongated tubular body part 111 and a terminal part 112. The protective cover further comprises an inner member 120 arranged inside and secured to the elongated tubular body part 111 so that both the outer member 110 and the inner member 120 are removed from the needle when a user grips the outer member 110. The terminal part 112 is arranged at the second end 140 of the protective cover 100 and the terminal part 112 has a widest width 190 larger than the widest width 191 of said elongated body part 111. The terminal part 112 is configured to allow a user to grip it and remove the protective cover 100 even when the body part is completely positioned inside a tubular protective element 192 such as a needle shield of an injection device (shown schematically in FIG. 1c).

By providing the protective cover with an outer member having a wide terminal part a protective cover for a needle that is easier to operate is provided.

The terminal part has a height 193 along the central axis 106 substantially shorter than the height of the elongated body part 194, in this embodiment, less than 5% of the height of the elongated body part 194. The widest width of the terminal part and the elongated body part 190 191 is measured in planes being perpendicular to the central axis 106. The terminal part 112 is formed as a plate extending in a plane being perpendicular to the central axis 106. The plate has a round shape. The terminal part 112 has a support surface 113 facing away from the needle (when the needle is inserted in the protective cover). The support surface 113 is configured to allow a hypodermic syringe connected to a needle arranged in the protective cover 100 to stand vertically. The support surface 112 is extending in a plane being perpendicular to the central axis.

FIG. 2a-c show a protective cover according to an embodiment of the present invention. FIG. 2a shows a side view of an inner member 220, FIG. 2b shows a side view of the assembled protective cover, and FIG. 2c shows a cross-section along the central axis 206 shown in FIG. 2b.

The protective cover 200 has a first opening 223 at a first end 230 for receiving the needle and a second end 240 opposite to the first end 230. The needle is inserted in the centre of the protective cover 200 along a central axis 206 of the protective cover 200. The protective cover 200 comprises an outer member 210 for allowing a user to grip the outer member 210 and remove the protective cover 200 from the needle. The outer member 210 has an elongated tubular body part 211 and a terminal part 212. The terminal part 212 is arranged at the second end 240 of the protective cover 200 and the terminal part 212 has a widest width 290 larger than the widest width 291 of said elongated body part 211. The terminal part 212 is configured to allow a user to grip it and remove the protective cover 200 even when the body part is completely positioned inside a tubular protective element. The terminal part 212 has a support surface 213 facing away from the needle (when the needle is inserted in the protective cover). The support surface 213 is configured to allow a hypodermic syringe connected to a needle arranged in the protective cover 200 to stand vertically. The support surface 213 is extending in a plane being perpendicular to the central axis. The protective cover further comprises an inner member 220 arranged inside and secured to the elongated tubular body part 211 so that both the outer member 210 and the inner member 220 are removed from the needle when a user grips the outer member 210. The inner member 220 is shown alone in FIG. 2a and together with the outer member 210 in FIG. 2b-c. The outer member 210 has two apertures 225 226 and the inner member 220 has a griping element 222 extending into the two apertures 225 226 of the outer member 210. Thus, the griping element 220 is configured to secure the inner member 220 to the outer member 210 so that both the outer member 210 and the inner member 220 are removed from the needle when a user pulls in the terminal part 212 of the outer member 210. The entire inner member 220 is made of a flexible material such as a rubber or a rubber like material. The gripping element 222 is a collar arranged at the top of the inner member 220. Thus, when the inner member 220 is inserted in the outer member 210, the collar 222 is deformed and parts of the collar are extending through two apertures 225 226. By using a collar as a gripping element the rotational orientation of the inner member 220 relative to the outer member 210 becomes insignificant, when the inner member 220 is inserted in the outer member 210. This makes the assembly of the protective cover easier.

FIG. 3a-c show a set comprising a protective cover and a hypodermic syringe according to an embodiment of the invention. FIG. 3a shows a perspective view, FIG. 3b shows a side view, and FIG. 3c shows a cross-section along the central axis 306 shown in FIG. 3b. The protective cover 300 has a first opening at a first end for receiving the needle and a second end opposite to the first end. The hypodermic syringe 360 has a body 371, a plunger 372, and a needle 373 attached to a needle hub 374. The needle 373 is inserted in the centre of the protective cover 300 along a central axis 306 of the protective cover 300. The protective cover 300 comprises an outer member for allowing a user to grip the outer member and remove the protective cover 300 from the needle 373. The outer member has an elongated tubular body part 311 and a terminal part 312. The terminal part 312 is arranged at the second end of the protective cover 300 and the terminal part 312 has a widest width 390 larger than the widest width 391 of said elongated body part 311. The terminal part 312 is configured to allow a user to grip it and remove the protective cover 300 even when the body part is completely positioned inside a tubular protective element such as a needle shield of an injection device. The terminal part 312 is formed as a plate extending in a plane being perpendicular to the central axis 306. The plate has a round shape. The terminal part 312 has a support surface 313 facing away from the needle.

The support surface 313 is configured to allow the hypodermic syringe 360 to stand vertically. The support surface 312 is extending in a plane being perpendicular to the central axis 306. The support surface 313 has a plurality of protruding elements 314 for preventing the support surface 313 from sliding.

FIG. 4a-b show a set comprising a protective cover, a hypodermic syringe and an injection device, according to an embodiment of the invention. FIG. 4a shows a perspective view and FIG. 4b shows a central cross-section. The hypodermic syringe 460 is identical to the hypodermic syringe 360 shown in FIG. 3a-c and the protective cover 400 is identical to the protective cover 300 shown in FIG. 3a-c. The injection device 480 comprises a housing for being positioned at the skin, a movable element 482 movably arranged relative to the housing between a retracted position and an injection position, and a spring 486 connecting the movable element 482 with the housing. In FIGS. 4a-b the movable element 482 is shown in the retracted position. The spring 486, when released, is configured to move the movable element 482 from the retracted position to the injection position. The movable element 482 comprises a hypodermic syringe holder 489 and the hypodermic syringe 460 is arranged therein. The housing comprises an elongated tubular main body 481 and a needle shield 483 attached to the elongated tubular main body 481. The injection device 480 comprises a release mechanism 484 for initiating an injection of the hypodermic syringe 460. The injection device 480 is configured so that when the movable element 482 is in the retracted position and the release mechanism 484 is pushed the movable element 482 moves to the injection position whereby the hypodermic syringe 460 is injected. The protective cover 400 has a first opening at a first end for receiving the needle and a second end opposite to the first end. The hypodermic syringe 460 has a body 471, a plunger 472, and a needle 473 attached to a needle hub 474. The needle 473 is inserted in the centre of the protective cover 400 along a central axis 406 of the protective cover 400. The protective cover 400 comprises an outer member for allowing a user to grip the outer member and remove the protective cover 400 from the needle 473. The outer member has an elongated tubular body part 411 and a terminal part 412. The terminal part 412 is arranged at the second end of the protective cover 400 and the terminal part 412 has a widest width 490 larger than the widest width 491 of the elongated body part 411. The terminal part 412 is formed as a plate extending in a plane being perpendicular to the central axis 406. The plate has a round shape. The terminal part 412 has a support surface 413 facing away from the needle. The needle shield 483 comprises a first opening 431 facing the skin of a user when the injection device 480 is positioned at the skin of the user. The housing comprises a planar contact surface 488 for being positioned at the skin of a user. The first opening 431 forms part of the planar contact surface 488. The terminal part 412 has a widest width 490 larger than the widest width 495 of the needle shield 483 at the first opening 431. The elongated body 411 of the protective cover 400 is partly arranged inside the needle shield, and the terminal part 412 is arranged outside the needle shield. This allows a user to easily grip the terminal part 412 and remove the protective cover 400 from the needle 473.

FIG. 5 illustrates a method of arranging a pre-filled hypodermic syringe in an injection device according to an embodiment of the invention. In the first step 561, a pre-filled hypodermic syringe 560 having a needle 573 with an inner member 520 of a protective cover arranged around it is obtained. Next, in step 562, an injection device 580 for injecting a hypodermic syringe along an injection direction defining an injection axis is obtained. The injection device 580 comprises a housing for being positioned at the skin, wherein the housing comprises an elongated main body 581 having a needle shield 583 attached. The needle shield 583 has a first opening 431 for facing the skin of the user and a second opening 432 opposite to the first opening 431. The injection device 580 further comprises a movable element 582 movably arranged relative to said housing between a retracted position and an injection position. The movable element 582 comprises a hypodermic syringe holder 489 for holding a hypodermic syringe. Then, in step 563, the pre-filled hypodermic syringe 560 is arranged in the hypodermic syringe holder 589 of the injection device 580, so that the inner member 520 is at least partly arranged inside the needle shield 583 of the injection device 580. Next, in step 564, an outer member 510 of the protective cover is obtained. The outer member 510 has a first end 530 and a second end 540 opposite to the first end 530. The outer member 510 comprises an elongated tubular body part 511 having an opening at the first end 530, and a terminal part 512 arranged at the second end 540. The terminal part 512 has a widest width larger than the widest width of the elongated tubular body part 511. Finally, in step 565, the outer member 510 is arranged around the inner member 520 by inserting the outer member 510 through the first opening 531 of the needle shield 583 so that the terminal part 512 is arranged outside the needle shield 583. The outer member 510 is configured to grip the inner member 520, whereby the inner member 520 is secured to the outer member 510. This allows a user to remove both the inner member 520 and the outer member 510 of the protective cover from the needle by pulling in the terminal part 512.

Consequently, an efficient method of arranging a pre-filled hypodermic syringe in an injection device is provided.

FIG. 6a-c show how a set comprising an injection device, a pre-filled hypodermic syringe, and a protective cover for a needle may be used according to an embodiment of the invention. FIG. 6a shows the set in a first state, where the pre-filled hypodermic syringe is attached to the injection device, the protective cover is arranged around a needle of the pre-filled hypodermic syringe, and the injection device is in a retracted position. When the set is in the first state, it is suitable for being stored or transported. FIG. 6b shows the set in a second state, where the pre-filled hypodermic syringe is attached to the injection device, the protective cover removed from the needle of the pre-filled hypodermic syringe, and the injection device is in a retracted position. In this state, the hypodermic syringe is ready to be injected by activating a release mechanism of the injection device. FIG. 6c shows the set in a third state, where the pre-filled hypodermic syringe is attached to the injection device, the protective cover removed from the needle of the pre-filled hypodermic syringe, and the injection device in an injected position. In this state, the hypodermic syringe is injected and its content may be provided to the patient by pushing the plunger. Afterwards, the movable element of the injection device may be retracted back into the retracted position by pulling in the handle of the movable element, whereby the needle again will be arranged inside the needle shield and the entire set may be removed from the patient. This allows a nurse or a doctor to perform the injection in a safe and controlled manner without risking to be stung by a contaminated needle.

FIG. 7a-e show an upper part of a hypodermic syringe holder 701 according to an embodiment of the invention. FIG. 7a shows a side view, FIG. 7b shows a bottom view, FIG. 7c shows a top view, FIG. 7d shows a perspective view, and FIG. 7e shows a front view. FIG. 8a-d show a lower part of a hypodermic syringe holder 802 according to an embodiment of the invention. FIG. 8a shows a side view, FIG. 8b shows a top view, FIG. 8c shows a perspective view, and FIG. 8d shows a front view. In the following referenced will be made to FIGS. 7-8. The upper part of the hypodermic syringe holder 701 is configured for mechanically engaging with the lower part 802, and together with the lower part surround a hypodermic syringe and prevent the hypodermic syringe from moving relative to a movable element of an injection device. In this embodiment the upper part 701 is completely separate from the lower part 801 (until the upper part is mechanically engaged with the lower part). However, in other embodiments, the upper part may be connected to the lower part via a hinge.

The upper part 701 is configured to mechanically engage with the lower part using a male/female locking mechanism 703 704 705 706 807 808 809 810 wherein the male part comprises one or more protruding member(s) 703 704 705 706 and the female part comprises one or more recess(es) and/or opening(s). In this embodiment, the upper part 701 is the male part and the lower part 802 in the female part. However, in other embodiments, the upper part may be the female part and the lower part may be the male part. The upper part 701 has a first side 730 and a second side 731 opposite to the first side 730. The first side 730 has two protruding members 703 704 and the second side 731 has two protruding members 705 706. Correspondingly, the lower part 802 has a first side 832 and second side 833 opposite to the first side 832. The first side 832 has two recesses 807 808 and the second side has two recess 809 810. By using four pairs of protruding members and recesses, rotational movement of a hypodermic syringe relative to the hypodermic syringe holder may more effectively be prevented.

In this embodiment, the protruding members of the upper part 703 704 705 706 are flexible protruding members configured to deform from a first shape to a second shape when the upper part 701 comes into contact with the lower part 802, and further to snap back into approximately the first shape when the flexible protruding member 703 704 705 706 are aligned with the recesses of the lower part 807 808 809 810, whereby the flexible protruding member 703 704 705 706 engages with the recesses 807 808 809 810 and locks the male part to the female part, allowing the upper part to be attached to the lower part by a pure translation between the two. The flexible protruding members 703 704 705 706 are shown in the first shape in FIG. 7a-e, and schematically in the second shape 724 725 in FIG. 7e. The male/female locking mechanism is configured to permanently mechanically engage the upper part 701 with the lower part 802 thereby preventing the upper part 701 from being disengaged with the lower part 801 without damaging the injection device (which the hypodermic syringe holder forms part of). Thus it may be secured that a single use injection device is not by mistake re-used.

Figure 9B:
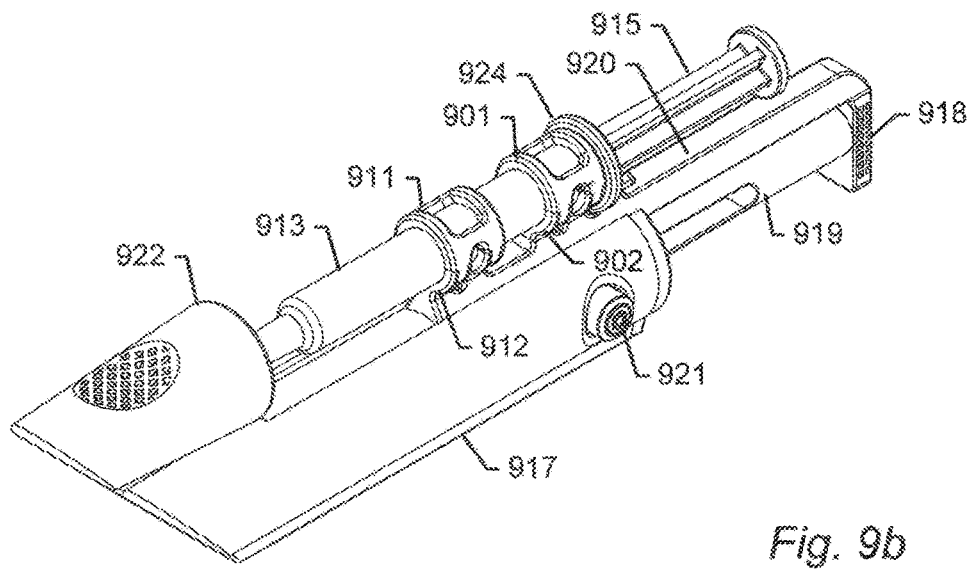
Figure 9C:
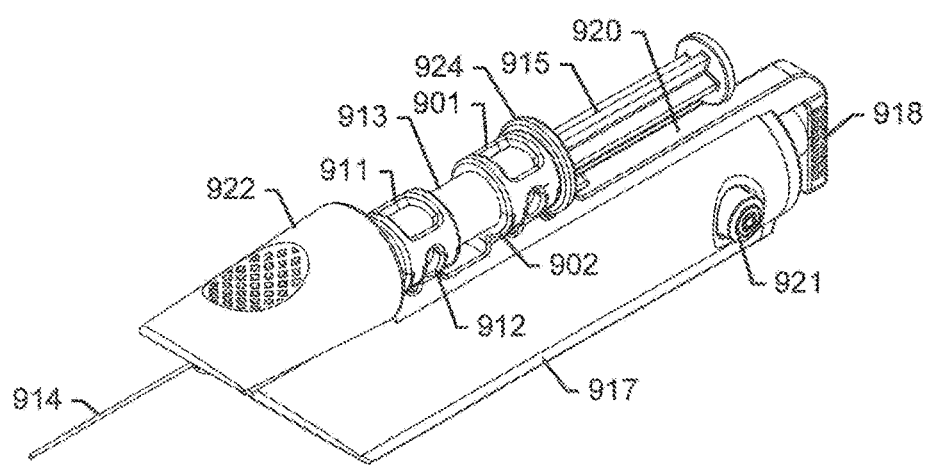

FIG. 9a-c show a set comprising an injection device 900 and a hypodermic syringe 913 914 915 924 according to an embodiment of the present invention. The injection device 900 is configured to inject the hypodermic syringe 919 914 915 924 along an injection direction defining an injection axis 923. The injection device 900 is configured to perform angled injections with an injection angle of 45 degrees. However, in other embodiments injection may be performed at other angles such as with an angle of 90 degrees (directly into the skin). The injection device 900 comprises a housing 917 922 for being positioned at the skin and a movable element 918 919 920. The movable element 918 919 920 is movably arranged relative to the housing 917 922 between an injection position (shown in FIGS. 9a and 9c) and a retracted position (shown in FIG. 9b). The movable element 918 919 920 comprises a hypodermic syringe holder 902 912 911 901 922 for holding a hypodermic syringe. The housing comprises a tubular element 917 and a tubular need shield 922. The movable element has a first portion 919 arranged to slide inside the tubular element 917, a second portion 920 arranged to slide outside the housing and a connection portion 918. The hypodermic syringe holder comprises a first upper part 901, a second upper part 911, a first lower part 902, and a second lower part 912. The second upper part 911 and the second lower part 912 are arranged with a distance to the first lower part 902 and the first upper part 901. The injection device may function in a similar manner as the injection device shown in FIG. 4a-b. The upper parts of the hypodermic syringe holder 901 911 are identical to the upper part 701 shown in FIG. 7a-e. Correspondingly, the lower parts of the hypodermic syringe holder 902 912 are identical to the lower part 802 shown in FIG. 8a-d. The hypodermic syringe holder comprises a groove 922 configured for receiving the collar 924 of said hypodermic syringe whereby said hypodermic syringe is prevented from moving relative to said movable element. The lower part of the hypodermic syringe holder 902 912 are attached to the second portion of the movable element 920. In this embodiment, the lower parts of the hypodermic syringe holder 902 912, the first portion 919, the second portion 920 and the connection portion 918 of the movable element are integrally moulded as a single element. In FIG. 9a the injection device 900 is shown with the upper parts of the hypodermic syringe holder 901 911 mechanically disengaged from the lower parts 902 912, whereas the injection device 900 in FIG. 9b-c is shown with the upper parts of the hypodermic syringe holder 901 911 mechanically engaged with the lower parts 902 912. By using two upper and lower parts, injection of large hypodermic syringes may safely be performed, without the hypodermic syringe becoming detached from the movable element and/or rotating with respect to the movable element.

FIG. 10a-e show an outer member 1010 of a protective cover according to an embodiment of the invention, where FIG. 10a shows a side view, FIG. 10b shows a front view, FIG. 10c shows a bottom view, and FIG. 1d-e show perspective views. FIG. 11a-b show an inner member of a protective cover according to an embodiment of the invention, where FIG. 11a shows a side view and FIG. 11b shows a perspective view. In the following reference will be made to FIGS. 10-11.

The outer member has an elongated tubular body part 1011 extending along a central axis 1006. The elongated tubular body part 1011 has a first set of apertures 1025 and a second set of apertures 2016 configured to receive a collar 1122 of the inner member. The elongated tubular body part 1011 comprises eight guiding protrusions 1096 protruding from an outer surface of the elongated tubular body part 1011 and extending along the central axis 1006. The guiding protrusions 1096 are configured to align the protective cover with a needle arranged inside a tubular needle shield of an injection device e.g. the guiding protrusions may be configured to interact with an inner surface of the needle shield whereby the protective cover may arranged around a needle. The outer element has a terminal part 1013 1098 1097 with a widest width larger than the widest width of the elongated tubular body part 1011. The terminal part comprises a plate 1013 having an inner surface facing the needle (when the needle is arranged in the protective cover) and an outer surface opposite to the inner surface, wherein said inner surface have a first portion and a second portion, said elongated tubular body part 1011 protrudes from said first portion, and said second portion surrounds said first portion and is configured to close an opening of a tubular needle shield of an injection device. The plate 1013 extends in a plane being perpendicular to the central axis 1006. The terminal part further comprises a wall 1098 protruding from the circumference of the plate 1013.

The wall 1098 have an inner surface for abutting an outer surface of an injection device and frictionally gripping said outer surface of said injection device (see FIG. 12), whereby the protective cover may be attached simultaneously to the needle and the injection device. The terminal part further comprises a handle 1097 protruding from the outer surface of the plate 1013. The handle may enable the protective cover to be both easier removed and re-inserted over the needle. By providing the handle on the outer surface of the plate of the terminal part, the exposure hazard for medical professionals may be reduced when the protective cover is re-insert over a used needle, as the plate will protect for droplets from the needle.

The plate 1013 has a widest width being at least 1.5 times larger than the widest width of the elongated tubular body part, and the handle 1097 is protruding with a distance to the central axis 106.

FIG. 12 shows a set comprising a protective cover 1200, a hypodermic syringe 1260 and an injection device 1280, according to an embodiment of the invention. The protective cover 1200 is identical with the protective cover shown in FIGS. 10-11.

The injection device 1280 comprises a housing 1281 for being positioned at the skin and a movable element 1282 movably arranged relative to the housing 1281 between a retracted position and an injection position. The movable element is shown in the retracted position in FIG. 12. The movable element 1282 comprises a hypodermic syringe holder 1289 for holding a hypodermic syringe. The injection device 1280 comprises further an injection depth modifying element 1240 configured to modify the injection depth of the injection device 1280. The injection depth modifying element 1240 enables the injection device to be used by a broader group of users and for a broader group of purposes.

The injection depth modifying element 1240 is movable relative to both the housing 1281 and the movable element 1282 and attachable at a first position to a selected element selected from the group of elements consisting of the movable element 1282 and the housing 1281 wherein when the injection depth modifying element 1240 is attached at the first position the movable element 1282 is limited to be movable relative to the housing 1281 between the retracted position and an intermediate position. Consequently, the injection depth is reduced. In this embodiment, the selected element is the movable element 1282 i.e. the injection depth modifying element 1240 is attachable at a first position of the movable element 1240. The injection depth modifying element 1240 is shown in the first position in FIG. 12, thus as long as the injection depth modifying element 1240 is attached to the movable element at the first position, the movable element 1282 is limited to be movable relative to the housing 1281 between the retracted position and an intermediate position. The injection depth modifying element 1240 may be identical to the injection depth modifying element shown in FIG. 13a-d. Alternatively, the injection depth modifying element 1240 may be identical to the injection depth modifying element shown in FIG. 14a-d.

The injection depth modifying element 1240 may be permanently attached to the movable element 1282 at the first position e.g. the injection depth modifying element 1240 may only be movable relative to both the housing 1281 and the movable element until it is attached at the first position. Alternatively, the injection depth modifying element 1240 may be non-permanently attached to the movable element 1282 at the first position.

In this embodiment the housing 1281 comprises: a tubular element having an upper opening; and the movable element 1282 comprises: a first portion arranged to slide inside the tubular element of the housing 1281, a second portion arranged to slide outside the housing 1281 and a connection portion connecting the first portion with the second portion, wherein the movable element 1282 extends out of the upper opening of the tubular element (similar to the injection device shown in FIG. 9). The housing 1281 comprises an upper surface 1242 facing away from the skin of the user (when the injection device is placed at the skin of a user); the injection depth modifying element 1240 comprises a lower surface 1241 facing the upper surface 1242 when the injection depth modifying element 1240 is attached at the first position and wherein the lower surface 1241 of the injection depth modifying element abuts the upper surface 1242 of the housing when the movable element is in the intermediate position (as shown in FIG. 15c).

Figure 16:
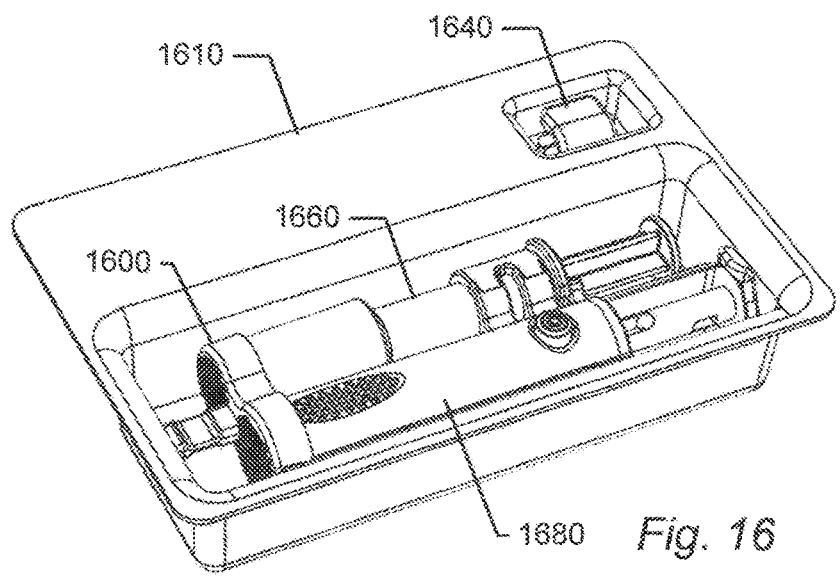
FIG. 16 shows a set of elements according to an embodiment of the present invention.

In this embodiment, the injection depth modifying element 1240 is movably arranged relative to both the housing 1281 and the movable element 1282 between a detached position, where the injection depth modifying element is provided separate from the housing and the movable element (as shown in FIG. 16), and the first position where the injection depth modifying element is attached to the movable element 1282.

FIG. 13a-d show an injection depth modifying element 1340 according to an embodiment of the invention, where FIG. 13a shows a perspective view, FIG. 13b shows a front view, FIG. 13c shows a top view and FIG. 13d shows a side view. The injection depth modifying element 1340 has a first gripping arm 1301 and a second gripping arm 1302 opposite to the first gripping arm 1301, the first gripping arm 1301 and the second gripping arm 1302 being connected by a connection portion 1303. The first gripping arm 1301 and the second gripping arm 1302 are configured to receive the selected element (the movable element or the housing) and attach the injection depth modifying element 1340 to the selected element.

FIG. 14a-d show an injection depth modifying element 1440 according to an embodiment of the invention, where FIG. 14a shows a perspective view, FIG. 14b shows a front view, FIG. 14c shows a top view and FIG. 14d shows a side view. The injection depth modifying element 1440 has a first gripping arm 1401 and a second gripping arm 1402 opposite to the first gripping arm 1401, the first gripping arm 1401 and the second gripping arm 1402 being connected by a connection portion 1403. The injection modifying element 1440 further comprises a male part 1404 of a male/female locking mechanism. The male part 1404 is fitted with barbs for providing a stronger connection between the male part and a female part. This may be especially advantageous when the injection device is a single use injection device.

The first gripping arm 1401, the second gripping arm 1402, and the male part 1404 are configured to receive the selected element (the movable element or the housing) and attach the injection depth modifying element 1440 to the selected element.

FIG. 15a-c illustrates how an injection depth modifying element as shown in FIG. 14a-d may be attached to a selected element according to an embodiment of the invention. In this embodiment the selected element is the movable element 1582. FIG. 15a shows the injection device 1580 with the injection depth modifying element 1540 provided separate from both the housing 1581 and the movable element 1582, and FIG. 15b-c show the injection device 1580 with the injection depth modifying element 1540 attached to the first position of the movable element 1540. The movable element 1582 is in the retracted position in FIG. 15a-b and in the intermediate position in FIG. 15c. The movable element 1582 comprises a female part 1583 (an opening) of a male/female locking mechanism. The female part 1583 is configured to receive the male part 1404 of the injection depth modifying element whereby the injection depth modifying element may be securely attached at the first position to the movable element 1582. The injection depth modifying element may simply be translated upwards as illustrated by the arrow 1584 to attach it to the movable element 1582.

FIG. 16 show a set of elements comprising an injection device 1680 having a housing and a movable element, a pre-filled hypodermic syringe 1660 having a needle, and a first injection depth modifying element 1640 movably arranged relative to both the housing and the movable element between a detached position, where the injection depth modifying element 1640 is provided separate from the housing and the movable element, and a first position where the injection depth modifying element 1640 is attached to the selected element. The set further comprises a protective cover 1600. The set is configured for single use and packaged in a protective environment 1610 closed by a plastic film.

Figure 17A:
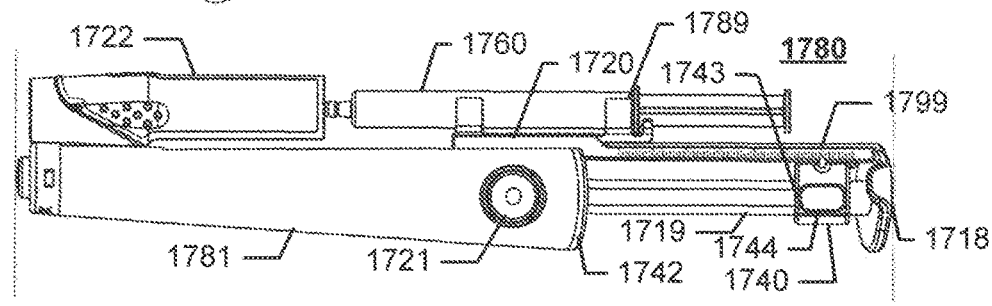
FIG. 17a-c show an injection device according to an embodiment of the present invention.
Figure 17B:
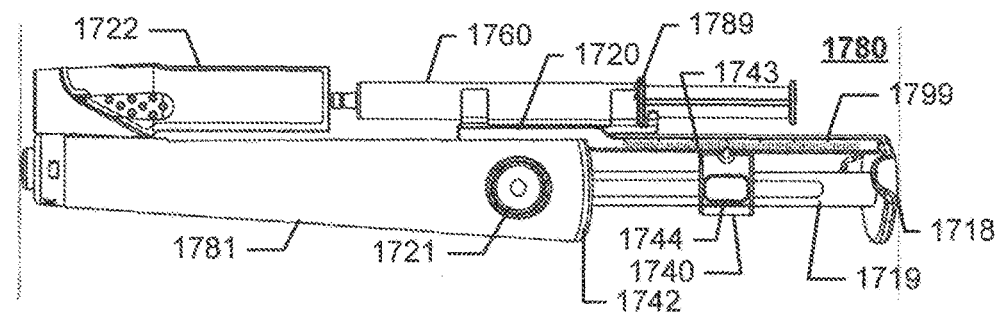
Figure 17C:
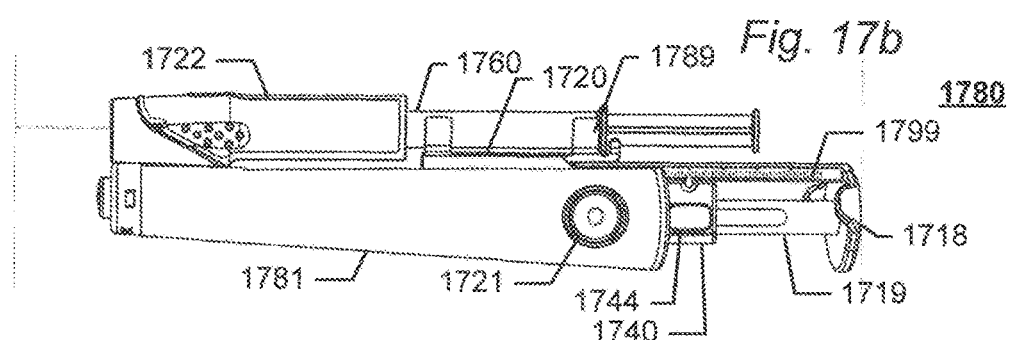

FIG. 17*a-c* show a set comprising a hypodermic syringe 1760 and an injection device 1780 according to an embodiment of the present invention. The injection device 1780 comprises a housing 1781 for being positioned at the skin and a movable element 1718 1719 1720 movably arranged relative to the housing 1781 between a retracted position and an injection position. The movable element 1718 1719 1720 comprises a hypodermic syringe holder 1789 for holding a hypodermic syringe. The injection device 1780 comprises further an injection depth modifying element 1740 configured to modify the injection depth of the injection device 1780. The injection depth modifying element 1740 enables the injection device to be used by a broader group of users and for a broader group of purposes.

The injection depth modifying element 1740 is movable relative to both the housing 1781 and the movable element 1718 1719 1720 and attachable at a first position to a selected element selected from the group of elements consisting of the movable element 1718 1719 1720 and the housing 1781 wherein when the injection depth modifying element 1240 is attached at the first position the movable element 1718 1719 1720 is limited to be movable relative to the housing 1781 between the retracted position and an intermediate position. This results in that the injection depth is reduced. In this embodiment, the selected element is the movable element 1718 1719 1720 i.e. the injection depth modifying element 1740 is attachable at a first position of the movable element 1718 1719 1720. The injection depth modifying element 1740 is shown in the first position in FIG. 17*b-c*, thus as long as the injection depth modifying element 1740 is attached to the movable element at the first position, the movable element 1718 1719 1720 is limited to be movable relative to the housing 7281 between the retracted position and the intermediate position. The movable element is shown in the retracted position in FIG. 17*a-b* and in the intermediate position in FIG. 17*c*. In this embodiment the housing 1781 comprises: a tubular element having an upper opening; and the movable element comprises: a first portion 1719 arranged to slide inside the tubular element of the housing 1781, a second portion 1720 arranged to slide outside the housing 1781, and a connection portion 1718 connecting the first portion 1719 with the second portion 1720 wherein the movable element 1718 1719 1720 extends out of the upper opening of the tubular element (similar to the injection device shown in FIG. 9). The housing 1781 comprises an upper surface 1742 facing away from the skin of the user (when the injection device is placed at the skin of a user); the injection depth modifying element 1740 comprises a lower surface 1743 facing the upper surface 1742 and wherein the lower surface 1243 of the injection depth modifying element abuts the upper surface 1742 of the housing when the movable element is in the intermediate position (as shown in FIG. 17*c*). In this embodiment the injection depth modifying element 1740 is non-permanently attached to the movable element 1718 1719 1720 at the first position and is further attachable to the movable element 1718 1719 1720 at a plurality of positions. The injection depth modifying element 1740 is permanently connected to the movable element 1718 1719 1720 and is movably arranged relative to the movable element 1718 1719 1720 along a first part movable element 1718 1719 1720 between a second position and the first position. Consequently, the injection depth may be selected with a high precision. The movable element is further provided with a scale 1799 for allowing a user to select a desired injection depth. The scale 1799 comprises a sequence of marks representing different injection depths.

The injection depth modifying element 1740 may comprise a first element 1740 for surrounding at least a part of movable element 1718 1719 1720, and a second element 1741 for attaching the first element 1740 to the movable element 1718 1719 1720, wherein the second element 1741 is movably arranged relative to the first element 1740 between an unengaged position and an engaged position, wherein the first element 1740 is movable relative to the movable element 1718 1719 1720 when the second element 1741 is in the unengaged position and attached to the movable element 1718 1719 1720 when the second element 1741 is in the engaged position.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. An injection device for injecting a hypodermic syringe along an injection direction defining an injection axis, wherein said injecting device comprises:
   a housing for being positioned at the skin, said housing comprising: a tubular element having an upper opening;
   a movable element movably arranged relative to said housing between a retracted position and an injection position, said movable element comprising: a hypodermic syringe holder for holding a hypodermic syringe, a first portion arranged to slide inside said tubular element of said housing, a second portion arranged to slide outside said housing and a connection portion connecting said first portion with said second portion, wherein said movable element extends out of said upper opening of said tubular element; and
   an injection depth modifying element configured to modify the injection depth of the injection device, wherein said injection depth modifying element is movable relative to both said housing and said movable element and being attachable at a first position to said movable element, wherein when said injection depth modifying element is attached at said first position, the movable element is limited to be movable relative to the housing between the retracted position and an intermediate position whereby the injection depth is reduced.

2. The injection device according to claim 1, wherein said housing comprises an upper surface facing away from the skin of the user; said injection depth modifying element comprises a lower surface facing said upper surface when said injection depth modifying elements is attached at said first position and wherein said lower surface of the injection depth modifying element abuts the upper surface of the housing when the movable element is in the intermediate position.

3. The injection device according to claim 1, wherein said injection depth modifying element is attachable to said selected element at a plurality of positions.

4. The injection device according to claim 1, wherein said injection depth modifying element is permanently connected to said selected element and is movably arranged relative to said selected element along a first part of said selected element between a second position and the first position.

5. The injection device according to claim 4, wherein said first part of said selected element is provided with a scale for allowing a user to select a desired injection depth.

6. The injection device according to claim 4, wherein the injection depth modifying element comprises a first element for surrounding at least a part of the selected element, and a second element for attaching the first element to the selected element, wherein the second element is movably arranged relative to the first element between an unengaged position and an engaged position, wherein the first element is movable relative to the selected element when the second element is in the unengaged position and attached to the selected element when the second element is in the engaged position.

7. The injection device according to claim 1, wherein said injection depth modifying element is movably arranged relative to both said housing and said movable element between a detached position, where the injection depth modifying element is provided separate from the housing and the movable element, and the first position where the injection depth modifying element is attached to the selected element.

8. The injection device according to claim 7, wherein the injection depth modifying element has a first gripping arm and a second gripping arm opposite to said first gripping arm, said first gripping arm and said second gripping arm being connected by a connection portion, wherein said first gripping arm and said second gripping arm are configured to receive said selected element and attach said injection depth modifying element to said selected element.

9. The injection device according to claim 8, wherein the injection depth modifying element is attachable to the selected element at the first position by a male/female locking mechanism.

10. The injection device according to claim 1, wherein said injection device further comprise a display, an input mechanism and an actuator, wherein said input mechanism is configured to allow a user to select a desired injection depth, said display is configured to display the selected injection depth and said actuator is configured to move said injection depth modifying element so that the selected desired injection depth results.

11. A set of elements comprising the injection device according to claim 1 and a pre-filled hypodermic syringe having a needle arranged in the hypodermic syringe holder of the injection device.

12. The set according to claim 11, wherein the set further comprises a first injection depth modifying element movably arranged relative to both said housing and said movable element between a detached position, where the injection depth modifying element is provided separate from the housing and the movable element, and the first position where the injection depth modifying element is attached to the selected element, wherein when said injection depth modifying elements is attached to said selected element, the movable element is limited to be movable relative to the housing between the retracted position and a first intermediate position.

13. The set according to claim 12, wherein the set further comprises a second injection depth modifying element movably arranged relative to both said housing and said movable element between a detached position, where the injection depth modifying element is provided separate from the housing and the movable element, and an attached position where the injection depth modifying element is attached to the selected element, wherein when said second injection depth modifying elements is attached to said selected element, the movable element is limited to be movable relative to the housing between the retracted position and a second intermediate position.

14. The set according to claim 11, wherein the set further comprises a protective cover, wherein the protective cover is arranged around the needle of the pre-filled hypodermic syringe.

15. The set according to claim 11, wherein the set is configured for single use and is packaged in a protective environment.

16. The set according to claim 11, wherein the set is packaged in a plastic box closed by a plastic film.

17. The injection device according to claim 1, wherein the injection device is configured to perform injections with an injection angle of 45 degrees.

18. The injection device according to claim 1, wherein said injecting device further comprises a needle shield attached to the upper opening of said tubular element so that a tip from a needle of the hypodermic syringe is fully arranged inside the needle shield when the movable element is arranged in the retractive position.

19. The injection device according to claim 1, wherein the hypodermic syringe holder comprises a first upper part and a corresponding first lower part and a second upper part and a corresponding second lower part, the first upper part and the second upper part being configured to be mechanically engageable with the corresponding first lower part and second lower part around a hypodermic syringe positioned in the hypodermic syringe holder to prevent detachment of the hypodermic syringe from the moveable element.

* * * * *